( 12 ) United States Patent
Inoue et al.

(10) Patent No.: US 9,186,676 B2
(45) Date of Patent: Nov. 17, 2015

(54) TEST REAGENT CONTAINER

(75) Inventors: Masahide Inoue, Chiba (JP); Minoru Asogawa, Tokyo (JP); Yoshinori Mishina, Saitama (JP)

(73) Assignees: Fujibo Holdings, Inc., Tokyo (JP); NEC Corporation, Tokyo (JP)

( * ) Notice: Subject to any disclaimer, the term of this patent is extended or adjusted under 35 U.S.C. 154(b) by 0 days.

(21) Appl. No.: 14/114,016

(22) PCT Filed: Apr. 20, 2012

(86) PCT No.: PCT/JP2012/060677
§ 371 (c)(1),
(2), (4) Date: Oct. 25, 2013

(87) PCT Pub. No.: WO2012/147636
PCT Pub. Date: Nov. 1, 2012

(65) Prior Publication Data
US 2014/0050636 A1 Feb. 20, 2014

(30) Foreign Application Priority Data

Apr. 25, 2011 (JP) ................................. 2011-097028

(51) Int. Cl.
*B01L 3/00* (2006.01)
*B65D 5/72* (2006.01)
*G01N 35/00* (2006.01)

(52) U.S. Cl.
CPC . *B01L 3/52* (2013.01); *B01L 3/523* (2013.01); *B65D 5/726* (2013.01); *B01L 3/5027* (2013.01);
(Continued)

(58) Field of Classification Search
CPC ... B01L 3/52; B01L 3/523; B01L 2300/0683; B01L 2300/044; B65D 5/54; B65D 5/726
See application file for complete search history.

(56) References Cited

U.S. PATENT DOCUMENTS 3,355,058 A 11/1967 Asbury
3,927,794 A 12/1975 Erdman
(Continued)

FOREIGN PATENT DOCUMENTS

DE 299 02 874 U1 6/1999
JP 63 191061 8/1988
(Continued)

OTHER PUBLICATIONS

International Search Report Issued Jun. 26, 2012 in PCT/JP12/060677 Filed Apr. 20, 2012.
(Continued)

*Primary Examiner* — Jill Warden
*Assistant Examiner* — Matthew Krcha
(74) *Attorney, Agent, or Firm* — Oblon, McClelland, Maier & Neustadt, L.L.P.

(57) ABSTRACT

A test reagent container including a discharge port, formed by depressing a projecting part formed on a container bottom part, through which content can be easily and reliably discharged. The test reagent container includes: a bottom part; a peripheral wall raised approximately perpendicularly from a periphery of the bottom part; and a storage part defined by the bottom part and peripheral wall. A projecting part is formed on the bottom part in a projecting manner toward outside the container. A proximal end of the projecting part is formed in a bendable manner relative to the bottom part, and an easily breakable part is formed on a periphery of the projecting part except for the proximal end of the projecting part. The easily breakable part is broken when the projecting part is depressed from outside the container to be pushed into the inside of the container to form a discharge port.

8 Claims, 5 Drawing Sheets

(52) U.S. Cl.
CPC ........ *B01L 2200/04* (2013.01); *B01L 2200/141* (2013.01); *B01L 2300/044* (2013.01); *B01L 2300/0819* (2013.01); *B01L 2300/0832* (2013.01); *B01L 2300/0851* (2013.01); *B01L 2400/0683* (2013.01); *G01N 35/00* (2013.01)

(56) References Cited

U.S. PATENT DOCUMENTS

| | | | |
|---|---|---|---|
| 4,769,333 | A | 9/1988 | Dole et al. |
| 4,784,283 | A | 11/1988 | Cantu |
| 5,304,348 | A | 4/1994 | Burd et al. |
| 5,523,986 | A * | 6/1996 | Ishii .......................... 369/13.17 |
| 2004/0241042 | A1 | 12/2004 | Pugia et al. |
| 2005/0272169 | A1 | 12/2005 | Griffin et al. |
| 2006/0245972 | A1 | 11/2006 | Osone et al. |
| 2010/0064781 | A1 * | 3/2010 | Cherubini et al. ........... 73/64.56 |
| 2011/0002812 | A1 | 1/2011 | Asogawa et al. |
| 2013/0312372 | A1 * | 11/2013 | Rodtness et al. ................ 53/476 |

FOREIGN PATENT DOCUMENTS

| | | |
|---|---|---|
| JP | 7 503794 | 4/1995 |
| JP | 2005 512071 | 4/2005 |
| JP | 2006 308366 | 11/2006 |
| JP | 2007 500850 | 1/2007 |
| JP | 2007 101200 | 4/2007 |
| WO | 2009 035062 | 3/2009 |

OTHER PUBLICATIONS

Extended Search Report issued Sep. 18, 2014 in European Patent Application No. 12777642.5.

* cited by examiner

TEST REAGENT CONTAINER

TECHNICAL FIELD

The present invention relates to a container for sealing a liquid, powdery or gaseous test reagent or the like, and more particularly to a test reagent container where a discharge port can be formed by depressing a projecting part formed on a bottom part of the container so that contents can be reliably discharged.

BACKGROUND ART

Recently, there have been researches on various liquid feeding mechanisms and methods where a filling container and ultrafine flow passages are formed on a piece of microchip, and a sample or a liquid specimen is fed and subjected to reaction under controlled conditions for a gene analysis, a blood examination or the like (patent literature 1).

In such an analysis or examination, it is crucial to prevent an artificial error such as the contamination of a sample or a specimen, an error in specimen injection or an error in an amount of test reagent. Particularly when a specimen is used in DNA identification or the like, reliability is required in injection of a specimen into an analyzer. To cope with such requirement, patent literature 2 discloses a specimen filling device for injecting a specimen into a microchip. The specimen filling device is mounted with a specimen package having a specimen chamber filled with a specimen, and when a projecting part formed on the specimen chamber is subjected to an external force, a portion of a bottom part is released, thereby discharging the specimen.

This specimen filling device is recognized as effective for preventing an artificial error such as contamination of a specimen, an error in specimen injection or an error in an amount of test reagent. However, the specimen filling device has the following drawback with respect to discharging of a specimen.

Specifically, when an external force is applied to the projecting part formed on a bottom part of the specimen chamber to break off the bottom part from a part to be broken around the projecting part, there is a possibility that the bottom part is deflected in the vicinity of the projecting part because the specimen chamber is formed of a material having resilience, thus only a portion of the part to be broken can break and other portions of the part remain unbroken, which means that a discharge port for discharging a specimen cannot be completely formed. Even when the discharge port could be completely formed, there still exists a possibility that a restoring force generated by resiliency acts to make the projecting part return to its original position and close the discharge port.

Further, in terms of ensuring a large discharge port, it is desirable to increase a height of the projecting part and deeply push the projecting part into the inside of the specimen chamber. In this case, however, at the time of inflating a film by compressed air to discharge a specimen to the outside as shown in FIG. 4(c) in patent literature 2, there exists a possibility that the inflation of the film is hindered by the projecting part pushed into the inside of the specimen chamber and the specimen cannot be sufficiently discharged to the outside.

LIST OF RELATED ART

Patent Literature

PTL 1: JP-A-2007-101200
PTL 2: WO 2009/035062

SUMMARY OF INVENTION

Technical Problem

Accordingly, the present invention aims to provide a test reagent container which can overcome the above-mentioned drawbacks of the conventional specimen container and can simply and reliably discharge the content.

Solution to Problem

The present invention has been made to achieve the above-mentioned aim, and provides a test reagent container which includes: a bottom part; a peripheral wall which is raised approximately perpendicularly from a periphery of the bottom part; and a storage part which is defined by the bottom part and the peripheral wall, wherein a projecting part is formed on the bottom part in a projecting manner toward the outside of the container, wherein a proximal end of the projecting part is formed in a bendable manner relative to the bottom part, and an easily breakable part is formed on a periphery of the projecting part except for the proximal end of the projecting part, a distal end side of the projecting part is positioned in the vicinity of the periphery of the bottom part, a portion of the projecting part where a projecting height from the bottom part becomes the greatest is positioned close to the periphery of the bottom part, and the easily breakable part is broken when the projecting part is depressed from the outside of the container, and the projecting part is pushed into the inside of the container so as to form a discharge port.

Advantageous Effects of Invention

According to the test reagent container of the present invention, the easily breakable part is broken when the projecting part formed on the bottom part is pushed from the outside of the container thus forming the discharge port for discharging the content. In this case, the easily breakable part of the projecting part can be reliably broken with a minimum necessary force to form the discharge port, and the content can be discharged effectively and reliably without obstruction by a broken portion of the discharge port closed due to restoring force and without hindrance to an operation of discharging the specimen to the outside by inflating the film caused by the projecting part penetrating into the inside of the container.

DESCRIPTION OF EMBODIMENTS

Hereinafter, embodiments of a test reagent container of the present invention are explained in detail in conjunction with drawings. However, the present invention is not limited to these embodiments.

Figure 1:
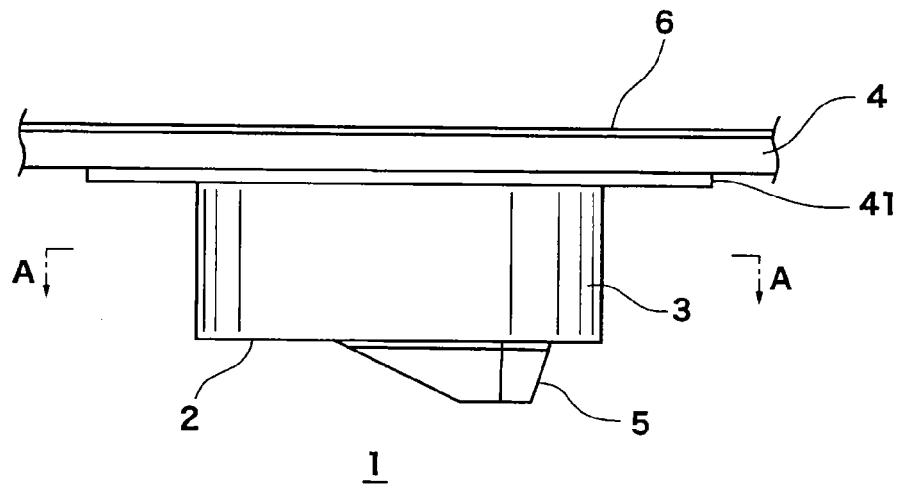
[FIG. 1] A side view of a test reagent container of the present invention.
Figure 2:
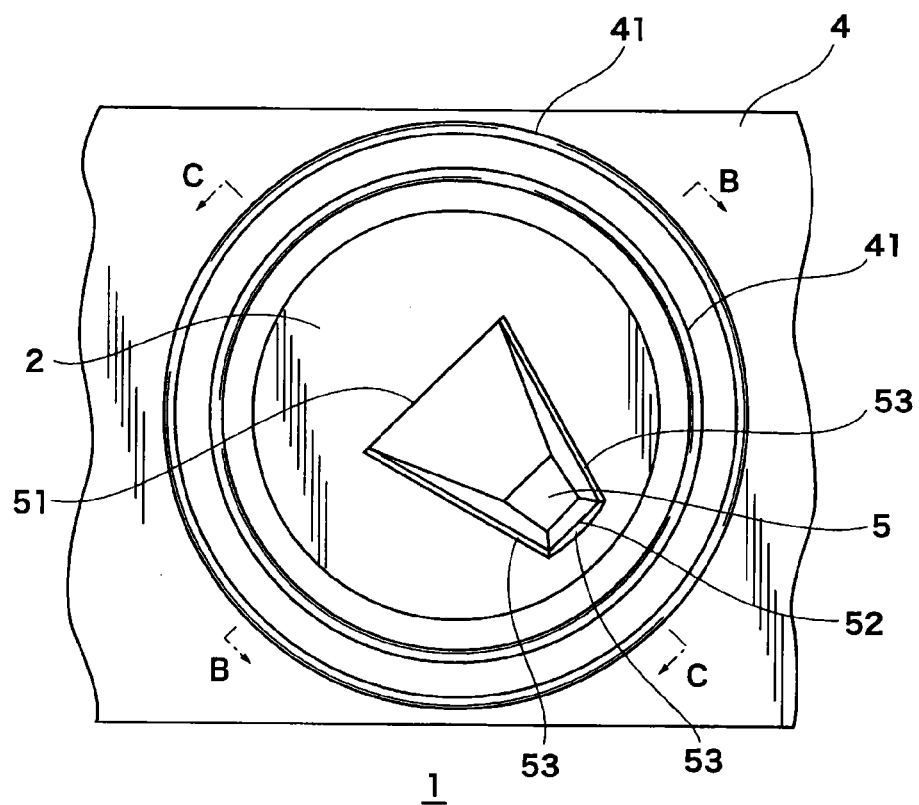
[FIG. 2] A bottom view of the test reagent container of the present invention.
Figure 3:
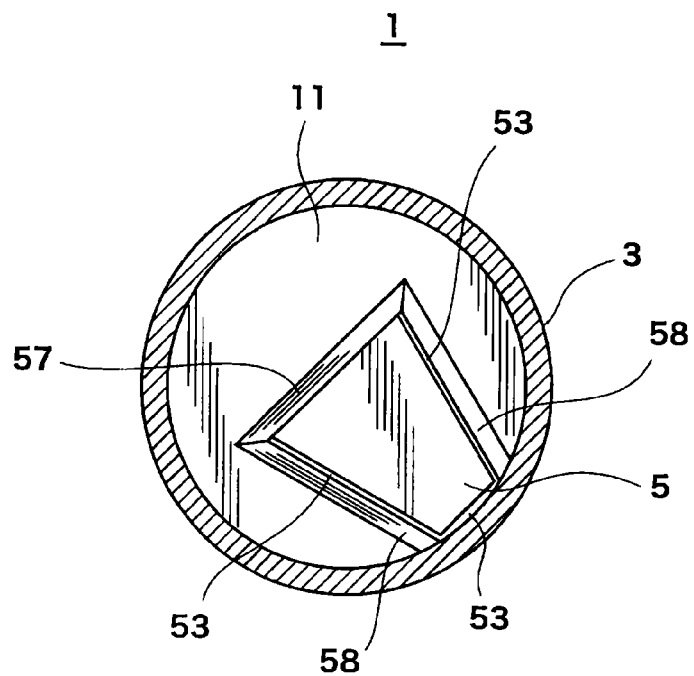
[FIG. 3] A cross-sectional view taken along a line A-A of the test reagent container of the present invention.
Figure 4:
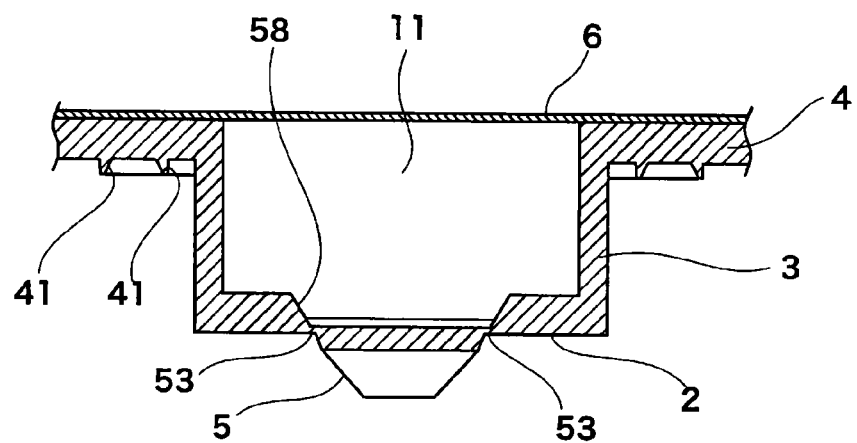
[FIG. 4] A cross-sectional view taken along a line B-B of the test reagent container of the present invention.
Figure 5:
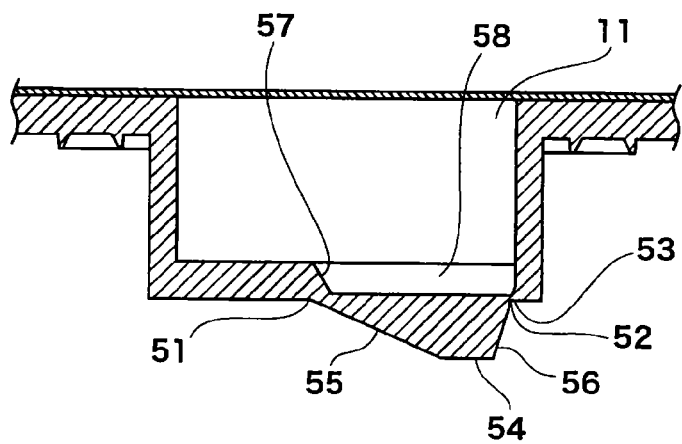
[FIG. 5] A cross-sectional view taken along a line C-C of the test reagent container of the present invention.

FIG. 1 is a side view of a test reagent container of the present invention, FIG. 2 is a bottom view of the test reagent container of the present invention, FIG. 3 is a cross-sectional view taken along a line A-A of the test reagent container of the present invention, FIG. 4 is a cross-sectional view taken along a line B-B of the test reagent container of the present invention, and FIG. 5 is a cross-sectional view taken along a line C-C of the test reagent container of the present invention. In the drawings, 1 indicates a test reagent container, 2 indicates a bottom part, 3 indicates a peripheral wall, 4 indicates a flange member, 5 indicates a projecting part, 6 indicates a film, 11 indicates a storage part, 41 indicates an annular projecting part, 51 indicates a proximal end of the projecting part 5, 52 indicates a distal end of the projecting part 5, 53 indicates an easily breakable part, 54 indicates a bottom surface, 55 indicates an inclined surface, 56 indicates an inclined surface, 57 indicates a stepped part, and 58 indicates a stepped part.

As shown in FIG. 1 to FIG. 5, the test reagent container 1 of the present invention is, as the basic constitution thereof, formed into a bottomed tray shape where the peripheral wall 3 is raised approximately perpendicularly from the periphery of the bottom part 2, and includes the storage part 11 defined by the bottom part 2 and the peripheral wall 3. The bottom part 2 is provided with the projecting part 5 which is formed in a projecting manner toward the outside of the container 1, and the plate-shaped flange member 4 is formed on an upper end of the peripheral wall 3 in a horizontally projecting manner. The film 6 which seals an opening part of the storage part 11 is adhered to an upper surface of the flange member 4.

The specific constitution of the test reagent container 1 of this embodiment is explained in detail hereinafter. The projecting part 5 is formed on the bottom part 2 of the test reagent container 1 in a downwardly projecting manner from the bottom part 2. As shown in FIG. 2, the projecting part 5 is formed into an approximately trapezoidal shape in a plan view where a proximal end 51 of the projecting part 5 forms a lower base of the trapezoidal shape and a distal end 52 of the projecting part 5 forms an upper base of the trapezoidal shape. While the proximal end 51 of the projecting part 5 is arranged in the vicinity of the center of the bottom part 2, the distal end 52 of the projecting part 5 is arranged in the vicinity of the periphery of the bottom part 2. Although the projecting part 5 of this embodiment is formed into an approximately trapezoidal shape as described above, a planar shape of the projecting part 5 is not limited to a trapezoidal shape, and may be formed into a semicircular shape including a semi-elliptical shape, a triangular shape, a quadrangular shape or the like. However, by forming the projecting part 5 into a shape having corners such as a trapezoidal shape, a triangular shape, a quadrangular shape or the like, the easily breakable part 53 can be reliably broken. Accordingly, it is more preferable to form the projecting part 5 into a shape having corners.

As shown in FIG. 5, the projecting part 5 is formed into a trapezoidal shape having unequal legs in longitudinal cross section. That is, the inclined surface 55 is formed on the projecting part 5 such that a projecting height of the projecting part 5 from the bottom part 2 is gradually increased from the proximal end 51 toward the distal end 52. A bottom surface 54 which is arranged horizontally parallel to the bottom part 2 is formed starting from a position approximately two thirds of a total length of the projecting part 5 away from the proximal end 51 to the distal end 52. Further, the inclined surface 56 which is inclined toward the distal end 52 from a portion in the vicinity of the distal end 52 is formed on the projecting part 5. In this manner, according to this embodiment, the projecting part 5 is formed into a trapezoidal shape having unequal legs where the bottom surface 54 which corresponds to the upper base of a trapezoidal shape is positioned close to the periphery of the bottom part 2. However, the cross-sectional shape of the projecting part 5 is not limited to such a shape, and may be other shape such as a triangular shape or a mountain shape having rounded corners as long as a portion of the projecting part 5 where the projecting height of the projecting part 5 from the bottom part 2 becomes the greatest is positioned close to the periphery of the bottom part 2. By forming the projecting part 5 such that the projecting height of the projecting part 5 is gradually increased toward the portion having the greatest height from the proximal end 51 side of the projecting part 5 as described above, the rigidity of the whole projecting part 5 is increased. Accordingly, there is no possibility that the projecting part 5 per se deflects when the projecting part 5 is pushed from the outside. Further, the bottom surface 54 is positioned close to the periphery of the bottom part 2 and hence, a stress generated by depressing concentrates on a distal end 52 side of the projecting part 5 so that the easily breakable part 53 is reliably broken. Thus such a constitution is preferable.

As shown in FIG. 3 to FIG. 5, the bottom part 2 has a sunken portion having a reduced wall thickness on which the projecting part 5 is formed, and stepped parts 57 and 58 are formed between such a portion and other portions of the bottom part 2. The respective stepped parts are formed in an inclined manner toward the peripheral wall. Due to such an inclination, even when a restoring force acts to make the projecting part 5 return to the original position after being pushed into the container, there is no possibility that broken portions of the projecting part 5 are brought into close contact with the stepped portions 57 and 58.

Portions formed between the periphery of the projecting part 5 except for the proximal end 51 and the stepped portions 58 or the peripheral wall 3 have a reduced wall thickness to form easily breakable parts 53 having a strength to such an extent that the parts can be broken by a pressure applied from the outside. A wall thickness of the portion formed between the proximal end 51 of the projecting part 5 and a lower end of the stepped part 57 is also reduced compared to other portions of the bottom part 2. That is, the portion has a strength to such an extent that it is not broken but is bendable with respect to the bottom part 2 when the projecting part 5 is depressed.

To reliably break the easily breakable parts 53 with a minimum necessary force, it is preferable to concentrate a stress on a specified portion. From this point of view, as in the case of this embodiment, it is desirable to form the projecting part 5 into an approximately trapezoidal planar shape and a trapezoidal shape having unequal legs in cross-section. That is, in a usual method for using the present invention, a pressure from the outside is transmitted to the projecting part 5 from the bottom surface 54 positioned close to the periphery of the bottom part 2 and hence, a stress concentrates on a distal-end 52 side of the projecting part 5. Since the projecting part 5 has an approximately trapezoidal planar shape, the force concentrates on two corner portions on both sides of the distal end 52, and breaking starts at such points. Thereafter, the easily breakable parts 53 are gradually broken along with depressing and, eventually, the easily breakable parts 53 can be reliably broken with a minimum necessary force.

Figure 6:
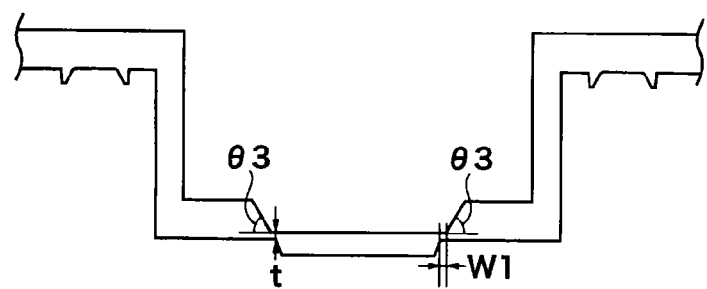
[FIG. 6] A cross-sectional view taken along the line B-B of the test reagent container of the present invention.
Figure 7:
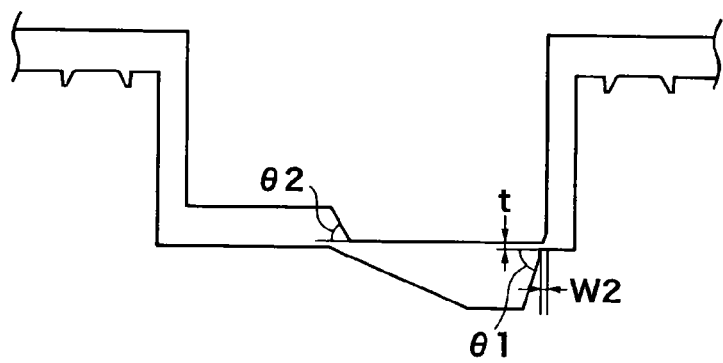
[FIG. 7] A cross-sectional view taken along the line C-C of the test reagent container of the present invention.

Further, to make such an effect more outstanding, it is preferable to set an inclination angle of the projecting part 5, inclination angles of the stepped parts 57 and 58 or a width of the easily breakable part 53 within the following ranges. To be more specific, as shown in FIG. 6 and FIG. 7, it is preferable to set the inclination angle $\theta 1$ of the inclined surface 56 on a projecting-part distal-end 52 side to a value which falls within a range of $45°≤\theta 1<90°$. By setting the inclination angle $\theta$ of the inclined surface 56 within the above-mentioned range, when the projecting part 5 is depressed, a stress concentrates on a distal end side of the projecting part 5 and hence, the easily breakable part 53 can be easily broken. At the same time, there is no possibility that the inclined surface 56 and the peripheral wall 3 interfere with each other when the projecting part 5 is pushed into the inside of the storage part 11. Accordingly, it is preferable to set the inclination angle $\theta$ of the inclined surface 56 within the above-mentioned range.

With respect to the inclination angles $\theta 2$ and $\theta 3$ of the stepped parts 57 and 58, it is preferable to set both inclination angles to values which fall within a range of $45°≤\theta<90°$. Due to such an inclination of the stepped parts, even when a restoring force acts to make the projecting part 5 return to the original position after being pushed into the inside of the storage part 11, there is no possibility that broken portions of the projecting part 5 are brought into close contact with the stepped portions 57 and 58.

To realize a strength in the easily breakable part 53 to such an extent that the easily breakable part 53 is broken by depressing the projecting part 5 with a minimum necessary force while preventing the easily breakable part 53 from being easily broken during storage under normal conditions, it is preferable to set a thickness t of the easily breakable part 53 to a value which falls within a range of $0.03<t≤0.2$ mm. With respect to widths w1 and w2 of the easily breakable parts 53, it is preferable to set the widths to values which fall within a range of $0≤w<1.0$ mm due to the substantially same reason.

A material of the container is not particularly limited as long as the material has necessary and sufficient sealing property for preserving a test reagent and a hardness to such an extent that the easily breakable part 53 is easily broken. As a material which satisfies these conditions, an EVA resin, a low-density PE or the like can be preferably used.

With respect to the film 6 which seals the opening of the storage part 11, it is preferable to use a film having a barrier property against an enzyme or a specific chemical such as an alcohol and having a stretching property to some extent. To be more specific, an EVOH film, a PE film, an LLDPE film or the like can be preferably used as the film 6. To further enhance a gas barrier property, a film having a barrier function may be laminated to the above-mentioned film in a peelable manner, and the film having a barrier function may be removed at the time of using the film 6. As such a film having a barrier function, an aluminum film or the like can be preferably used.

Figure 8:
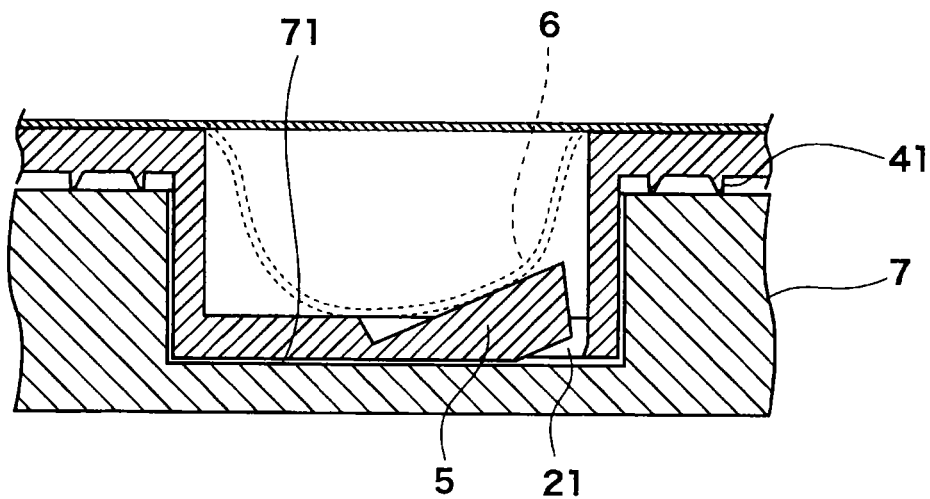
[FIG. 8] A view showing one mode of a use state of the test reagent container of the present invention.

FIG. 8 shows one mode of a use state of the test reagent container according to the present invention. The test reagent container 1 filled with a test reagent is mounted in a cartridge 7 for analysis such as a microchip. A recessed part 71 in which the test reagent container 1 can be mounted is formed in the cartridge 7, and a groove portion for delivering a test reagent from a bottom part of the recessed part 71 is formed on the cartridge 7 in an extending manner (not shown in the drawing). The recessed part 71 has a depth equal to or substantially equal to a height of the peripheral wall 3 of the test reagent container 1. Hereinafter, a series of flow of an operation of mounting the test reagent container 1 is explained. Firstly, the test reagent container 1 is inserted into the inside of the recessed part 71 from a bottom part 2 side as it is. Alternatively, when a film having a barrier function is laminated to the film 6, the film having a barrier property is removed from the film 6 and the test reagent container 1 is inserted into the inside of the recessed part 71 from a bottom part 2 side. At this point in time, the test reagent container 1 is not completely inserted due to the projecting part 5 in contact with the bottom part of the recessed part 71 and hence, a gap is formed between the bottom part 2 of the test reagent container 1 and the recessed part 71. Next, the test reagent container 1 is covered with a cover member or the like from above, and a downward pressure is applied to the test reagent container 1. Due to such depressing, an upward stress acts on the projecting part 5 in contact with the bottom part of the recessed part 71, thereby breaking the easily breakable part 53 formed on the periphery of the projecting part 5. As a result, the projecting part 5 is inserted into the inside of the storage part 11 while being bent at the proximal end 51. Then, the test reagent container 1 is further deeply inserted into the inside of the recessed part 71, and the mounting operation is completed at the point of time that the bottom part 2 is brought into contact with the bottom part of the recessed part 71 (FIG. 8).

In this manner, at the time of mounting the test reagent container 1 in the analyzer 7, the easily breakable part 53 is broken so that a discharge port 21 for discharging a test reagent which is the content is formed, and the test reagent is delivered from the groove part. Although the content may be discharged in such a manner that the content flows out naturally, to more effectively discharge a test reagent without leaving the test reagent in the storage part 11, it is preferable to forcibly discharge the content by applying an air pressure to the film 6 from above thus inflating the film 6 in the inside of the storage part 11. The film 6 subjected to the air pressure is inflated in a shape which approximately conforms to a shape of the inside of the storage part 11 (indicated by a dotted line in FIG. 8). In this case, with respect to the projecting part 5 of the present invention, a projecting-part distal-end 52 is formed in the vicinity of the periphery of the bottom part 2 and hence, even when the projecting part 5 is inserted into the inside of the storage part 11 while being bent, the projecting part 5 does not obstruct the inflation of the film 6 whereby the content can be discharged more effectively.

Further, in the test reagent container 1 of this embodiment, annular projecting parts 41 are formed on a lower surface of the flange member 4 in a state where the annular projecting parts 41 surround the peripheral wall 3 doubly. Peak portions of the annular projecting parts 41 are brought into contact with a ceiling surface of the cartridge 7 when the test reagent container 1 is completely inserted into the recessed part 71. Thus, even when the content exudes through a fine gap between the test reagent container 1 and the recessed part 71 by a chance, the content is sealed at the annular projecting parts 41 and hence, the contamination of a test reagent or the like can be effectively prevented without using a sealing member such as an O ring. To further enhance such a sealing effect, a film made of an elastic raw material such as a silicon film (not shown in the drawing) may be laminated to the ceiling surface of the cartridge 7. By laminating such an elastic film to the ceiling surface of the cartridge 7, when the test reagent container 1 is mounted in the cartridge 7, the peak portions of the annular projecting parts 41 bite into the elastic film and hence, the sealing property of the annular projecting parts 41 can be further enhanced. Further, separately from the annular projecting parts 41 or together with the annular projecting parts 41, an annular projecting part (not shown in the drawing) which circumferentially surrounds an outer peripheral surface of the peripheral wall 3 of the test reagent container 1 may be formed. Thus, even when the content exudes through a fine gap formed between the test reagent container 1 and the recessed part 71, the content is sealed at the annular projecting part. Accordingly, it is preferable to form such an annular projecting part.

The test reagent container 1 according to the present invention may be configured such that a plurality of containers 1 are contiguously provided. In such a case, the containers arranged adjacent to each other may be interconnected by a flange member 4. For example, to provide a five-tandem container, five test reagent containers 1 are joined with each other using a sheet of flange member 4. The five-tandem container may be used in such a manner that four containers among these containers are filled with a test reagent in advance, and the fifth container is filled with a collected sample.

Figure 9:
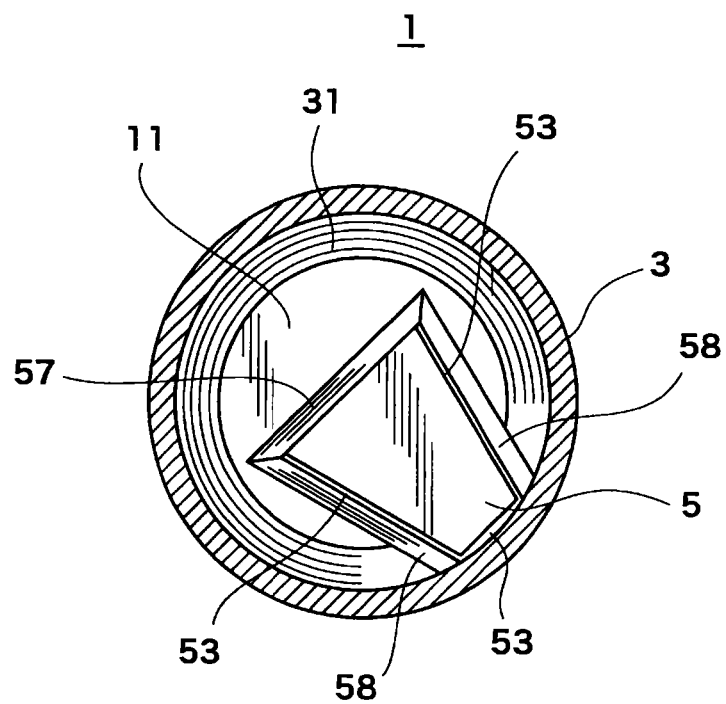
[FIG. 9] A cross-sectional view taken along a line A-A showing a different embodiment of the test reagent container of the present invention.
Figure 10:
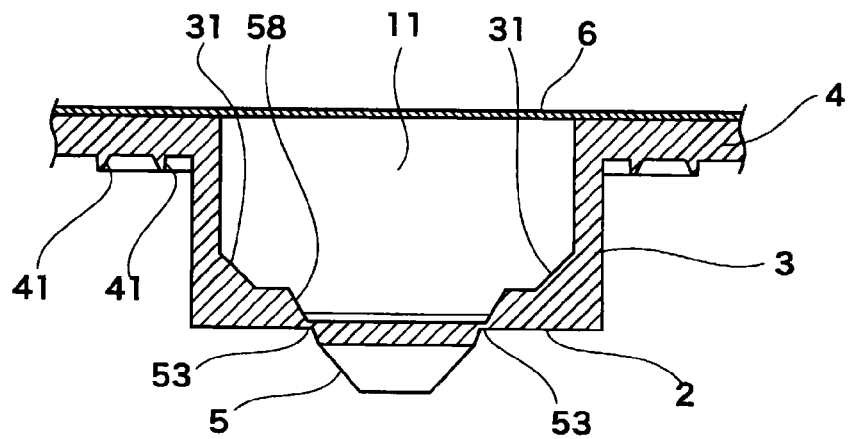
[FIG. 10] A cross-sectional view taken along a line B-B showing a different embodiment of the test reagent container of the present invention.
Figure 11:
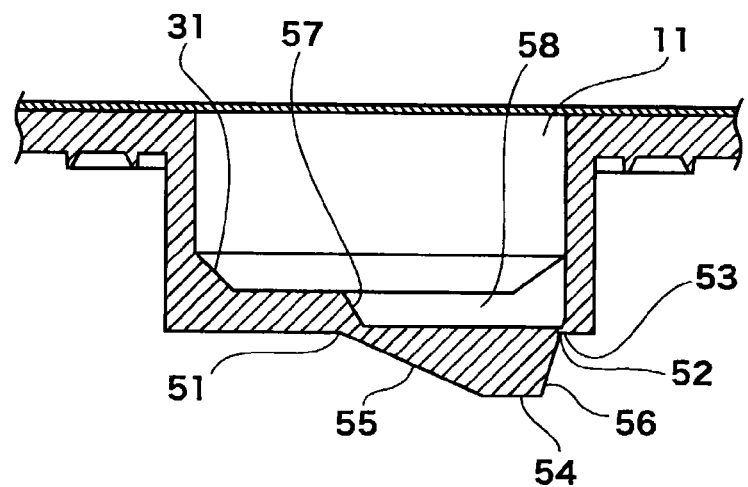
[FIG. 11] A cross-sectional view taken along a line C-C showing a different embodiment of the test reagent container of the present invention.

FIG. 9 to FIG. 11 show test reagent containers according to different embodiments of the present invention. As shown in each drawing, in the test reagent container 1 of each embodiment, a tapered part 31 having an inclined surface is formed on an inner corner portion where a peripheral wall 3 and a bottom part 2 abut each other. By forming the tapered part 31 on the inner corner portion between the peripheral wall 3 and the bottom part 2, when a film 6 is inflated by an air pressure in the inside of a storage part 11 as indicated by a dotted line in FIG. 8, the film 6 adheres to an inner wall surface of the storage part 11 without forming a gap, thereby making it possible to completely discharge a test reagent which is liable to remain at the inner corner portion between the peripheral wall 3 and the bottom part 2. As a result, it is no longer necessary to take into account an amount of liquid remaining in the test reagent container and hence, the adjustment of an amount of liquid can be performed more accurately.

Further, the test reagent container of this embodiment enhances the rigidity of the whole bottom part 2 by forming the tapered part 31, thereby reducing the possibility that the bottom part 2 is deflected to disperse a stress applied to the projecting part 5 from the outside. Therefore, the stress can be concentrated on an easily breakable part 53 and achieve more reliable breaking of the easily breakable part 53.

INDUSTRIAL APPLICABILITY

The test reagent container of the present invention is most preferably applied to the content in a liquid form. However, the test reagent container of the present invention is also applicable to the content in other forms such as a powdery form and a gaseous form. Further, the use of the test reagent container of the present invention is not limited to the filling of a test reagent into an analyzing/inspection device, and the test reagent container of the present invention can be used widely as long as the property that the content is reliably discharged by depressing from the outside can be utilized.

REFERENCE SIGNS LIST

1: test reagent container
2: bottom part
3: peripheral wall
4: flange part
5: projecting part
6: film
7: cartridge for analysis
11: storage part
21: discharge port
31: tapered part
41: annular projecting part
51: proximal end
52: distal end
53: easily breakable part
54: bottom surface
55: inclined surface
56: inclined surface
57: stepped part
58: stepped part
71: recessed part
$\theta 1$: inclination angle of inclined surface 56
$\theta 2$: inclination angle of stepped part 57
$\theta 3$: inclination angle of stepped part 58
t: thickness of easily breakable part
w1: width of easily breakable part
w2: width of easily breakable part

The invention claimed is:
1. A test reagent container comprising:
a bottom part;
a peripheral wall which is raised approximately perpendicularly from a periphery of the bottom part to define a storage part formed by the bottom part and the peripheral wall; and
a projecting part formed on the bottom part and having a boundary where the projecting part connects with the bottom part and begins to protrude in a projecting manner from the bottom part toward an outside of the container, the projecting part comprising a proximal end which forms a portion of the boundary and is bendable relative to the bottom part, a distal end side of the projecting part is positioned in the vicinity of the periphery of the bottom part, and an easily breakable part formed on said boundary except for the proximal end and including the distal end, wherein:
a portion of the bottom part of the container defined by said boundary of the projecting part has a reduced wall thickness compared to other portions of the bottom part, and a stepped part which is inclined toward the periphery of the bottom part is formed on at least part of said boundary of the projecting part,
a portion of the projecting part where a projecting height from the bottom part becomes the greatest is positioned close to the periphery of the bottom part and the projecting height of the projecting part from the bottom part is gradually increased from the proximal end of the projecting part to the distal end of the projecting part,
the easily breakable part is broken when the projecting part is depressed from the outside of the container, and the projecting part is pushed into the inside of the container so as to form a discharge port, and
a flange member is formed on an upper end of the peripheral wall in a projecting manner, a container opening part is sealed by laminating a film onto an upper surface of the flange member, and a pressure is applied to the film from the outside so that the film is inflated into the inside of the storage part thus discharging the content.
2. The test reagent container according to claim 1, wherein the projecting part is formed into a shape selected from a group of shapes consisting of a trapezoidal shape, a quadrangular shape and a triangular shape in a plan view.

3. The test reagent container according to claim 1, wherein the projecting part is formed in an trapezoidal shape having unequal legs in a center longitudinal cross-sectional view, and a bottom surface of the projecting part which corresponds to an upper base of the trapezoidal shape is positioned close to the periphery of the bottom part.

4. The test reagent container according to claim 1, wherein an inclination angle of a distal-end-side inclined surface of the projecting part in the center longitudinal cross-sectional view is set to a value which falls within a range of $45° \leq \theta < 90°$.

5. The test reagent container according to claim 1, wherein the inclination angle of the stepped part is set to a value which falls within a range of $45° \leq \theta < 90°$.

6. The test reagent container according to claim 1, wherein a width of the easily breakable part is set to a value which falls within a range of $w < 1.0$ mm, and a thickness of the easily breakable part is set to a value which falls within a range of $0.03 < t \leq 0.2$ mm.

7. The test reagent container according to claim 1, wherein an annular projecting part is formed on a lower surface of the flange member around the peripheral wall.

8. The test reagent container according to claim 1, wherein a tapered part is formed on an inner corner part where the bottom part and the peripheral wall abut each other.

* * * * *